United States Patent
Lunsford et al.

(10) Patent No.: US 7,735,525 B2
(45) Date of Patent: Jun. 15, 2010

(54) THERMALLY INSULATED APPARATUS FOR LIQUID CHROMATOGRAPHIC ANALYSIS

(75) Inventors: Morlan H. Lunsford, Thousand Oaks, CA (US); Julian S. Osaki, Thousand Oaks, CA (US); Glen J. Salle, Camarillo, CA (US); Christopher C. Corpuz, Camarillo, CA (US)

(73) Assignee: Amgen Inc., Thousand Oaks, CA (US)

( * ) Notice: Subject to any disclaimer, the term of this patent is extended or adjusted under 35 U.S.C. 154(b) by 525 days.

(21) Appl. No.: 11/559,809

(22) Filed: Nov. 14, 2006

(65) Prior Publication Data
US 2007/0175270 A1    Aug. 2, 2007

Related U.S. Application Data

(60) Provisional application No. 60/736,496, filed on Nov. 14, 2005.

(51) Int. Cl.
*F16L 9/00* (2006.01)
(52) U.S. Cl. .................. 138/177; 138/148; 138/89; 138/96 R; 138/109
(58) Field of Classification Search .............. 138/109, 138/137, 140, 141, 149, DIG. 1, 96 R, 96 T, 138/89; 428/36.91
See application file for complete search history.

(56) References Cited

U.S. PATENT DOCUMENTS

| 3,273,597 | A * | 9/1966 | Reznor ................... 138/30 |
| 4,019,372 | A | 4/1977 | Parkell et al. ............ 73/61.57 |
| 4,100,827 | A * | 7/1978 | Flemming ................ 82/163 |
| 4,560,012 | A * | 12/1985 | McNeely, Jr. ............ 175/61 |
| 6,601,439 | B2 | 8/2003 | Choikhet et al. .......... 73/61.57 |
| 6,666,074 | B2 | 12/2003 | Gerner et al. ............ 73/61.52 |
| 7,101,477 | B1 * | 9/2006 | Willis et al. ............ 210/198.2 |
| 2007/0084982 | A1 * | 4/2007 | Martone et al. ........ 248/316.8 |

* cited by examiner

*Primary Examiner*—Patrick F Brinson
(74) *Attorney, Agent, or Firm*—John A. Lamerdin

(57) ABSTRACT

A thermally insulated apparatus provides a substantially adiabatic environment for elevated temperature liquid chromatography applications. The thermally insulated apparatus minimizes or eliminates temperature gradients between columns and mobile phases, and maintains a temperature at or near the set point of an operably coupled heating means. The apparatus is also effective when used in conjunction with a liquid mobile phase heater such as those provided by an HPLC column compartment or a metal capillary of sufficient length to heat the liquid mobile phase.

6 Claims, 1 Drawing Sheet

THERMALLY INSULATED APPARATUS FOR LIQUID CHROMATOGRAPHIC ANALYSIS

CROSS-REFERENCE TO RELATED APPLICATIONS

This application claims the benefit of U.S. Provisional Application No. 60/736,496 filed Nov. 14, 2005 which is hereby incorporated by reference herein.

FIELD OF THE INVENTION

The invention relates generally to liquid chromatography systems, columns, and assays. More particularly, the invention relates to a thermally insulated apparatus that provides improved thermal stability for liquid chromatographic columns during separation and/or analysis at elevated temperatures.

BACKGROUND OF THE INVENTION

A number of liquid chromatography systems utilize a variety of configurations specifically tailored to particular chromatographic applications. In many liquid chromatographic systems, elevated temperatures are helpful for the analysis and resolution of liquid samples, or dissolved solutes, in mobile phases. Generally, increased liquid mobile phase temperature reduces mobile phase viscosity resulting in increased mobile phase flow rates through the stationary phase. Elevated temperature can also maintain or improve the resolution and elution profiles of chromatographic separations and assays. As a result, a number of liquid chromatography systems in use today utilize heating means for elevating the assay temperature, including mobile phase temperature, as the mobile phase is directed through the chromatography system.

Chromatographic heating systems in use today are generally operated around 80° C. or below, and have several characteristics which compromise the overall efficacy of elevated temperature liquid chromatography. Some existing systems utilize conductive or convective heating means directed to the chromatographic column to impart heat energy to the mobile phase for elevated temperature analysis of dissolved samples/analytes. Such techniques fail to properly "pre-heat" the mobile phase prior to application onto, or injection into, the chromatographic column, which generates mobile phase temperature profile gradients radially and axially within the chromatographic column. Mobile phase temperature gradients are, in general, undesired in liquid chromatography applications because it can result in loss of resolution and peak broadening. This problem has been addressed by a number of methods, most notably mobile phase pre-heaters that are designed to heat mobile phase to a desired temperature prior to application onto the chromatographic column. These systems are largely inefficient because the temperature of the pre-heated mobile phase is typically measurably different than the temperature of the chromatography system, which can create undesirable temperature gradients within the column.

Some chromatographic heating systems utilize a radiant or convective oven, which can house one or more of the chromatographic system components in order to elevate the temperature of the mobile phase being transported to the column, as well as the column itself. Such ovens are typically large in size and have minimal success in elevating temperatures uniformly. For example, the desired set temperature may not be reached in all locations within the oven, which creates temperature gradients within regions of multi-component chromatographic systems depending upon the position of each component within the oven. This can result in large temperature differences between the set point and even the external temperature of the chromatographic column of over 20° C. (±2° C.). Further, the temperature within the chromatographic column can vary both radially and axially, due to differences in temperature of the incoming mobile phase, as compared to that of the oven and/or the column separation media (stationary phase). Thus, a common problem experienced with oven heating systems is that the column temperature varies from the desired temperature set point, due either to temperature gradients within the oven, ineffective thermal transfer, and/or slow thermal equilibration of the column under actual operating conditions.

Thus, there remains a need in the art for an insulator that maintains consistent heat over the entirety of the chromatographic column, so as to minimize temperature gradients between pre-heated mobile phase and the column media, as well as axial and radial temperature gradients within the column itself. Such insulators can also maintain a desired column set point temperature during a chromatographic experiment throughout the chromatographic column. The present invention provides an economical thermally insulated apparatus for efficiently and effectively insulating a chromatographic column for assays and separations performed at elevated temperatures.

SUMMARY OF THE INVENTION

In one aspect, the invention provides a thermally insulated apparatus for liquid chromatographic separation columns, wherein the thermally insulated apparatus reduces or eliminates temperature gradients over the radial and longitudinal dimensions of the chromatographic column.

In another aspect, the invention provides a thermally insulated apparatus for liquid chromatographic separation columns, wherein the thermally insulated apparatus reduces or eliminates differences between the desired thermal set point and the actual column temperature.

In yet another aspect, the invention provides a liquid chromatographic separation column equipped with a thermally insulated apparatus as herein described.

In additional aspects, the invention relates to methods of maintaining a temperature setting during a chromatographic experiment (assay) comprising a thermally insulated apparatus for liquid chromatographic separation columns.

DETAILED DESCRIPTION OF THE PREFERRED EMBODIMENTS

Figure 1A:
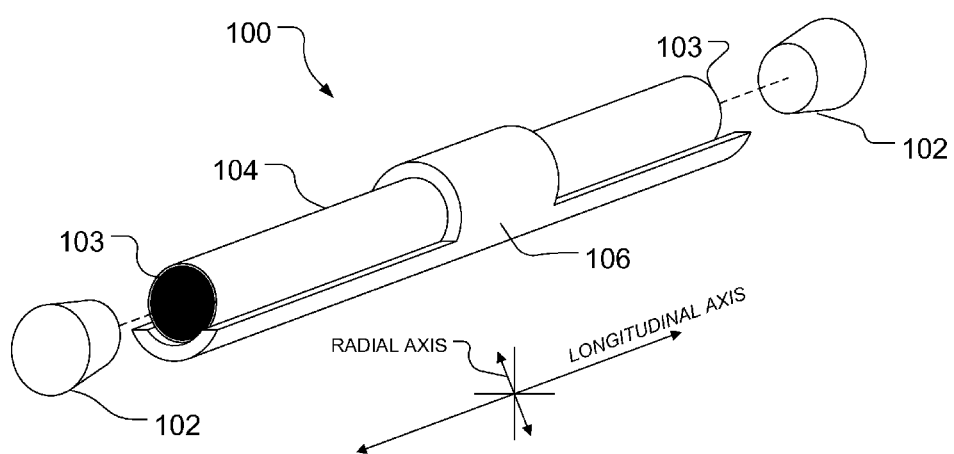
FIG. 1A depicts one embodiment of the thermally insulated apparatus (100) of the invention. The elongated metallic body (104) in this embodiment is cylindrical with longitudinal and radial axes. Two openings (103) are located at opposing ends of the longitudinal axis of the metallic body. Insulating material (106) contacts the outer surface of the metallic body (104), and completely encircles or surrounds it over at least some of the length. In other portions of the length, the metallic body (104) does not contact the insulating material (106), which allows metallic body (104) to contact an external heating source. The end caps (102) cover openings (103).
Figure 1B:
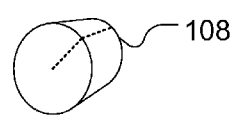
FIG. 1B depicts the end caps or capping members (102) that comprise an opening (108) in the form of a slit, through which tubing carrying mobile phase and/or sample can pass to and from the chromatography column.

The following detailed description of various aspects and advantages of the invention is intended to be representative of various possible configurations and embodiments of the invention. Those of ordinary skill in the art will be able to envision and recognize other embodiments of the invention that fall within the scope of the invention.

In one aspect, the invention provides a thermally insulated apparatus for liquid chromatographic separation columns, wherein the thermally insulated apparatus reduces or eliminates temperature gradients over the radial and longitudinal dimensions of the chromatographic column. The thermally insulated apparatus comprises (a) an elongated metallic body having a hollow interior portion, with two openings located at opposing ends of the length of the elongated body; and (b) an insulating material contacting the outer surface of the metallic member of (a). The thermally insulated apparatus can take a number of various shapes, but typically has proportions that are similar to the proportions of the column for which it is designed. The thermally insulated apparatus comprises a hollow interior portion that has a shape that is large enough to accommodate the particular column that is to be insulated. The particular cross-section or profile shape, which as used herein refers to the shortest dimension of the elongated body (diameter) of the thermally insulated apparatus can vary widely, including such non-limiting shapes as triangular; circular; square; rectangular; polygonal, such as pentagonal, hexagonal, heptagonal, octagonal, nonagonal, decagonal, or dodecagonal, and the like; starburst/sunburst (i.e., an arrangement of fin- or cog-like projections from a central, continuous shape, cylindrical, and tubular. The hollow interior portion can comprise either a different or the same shape profile as the outer surface of the metallic body; for example, the metallic body can have a square profile, while the hollow interior portion can have a circular profile. As long as at least some of the surface of the hollow interior portion can contact the outer surface of the chromatographic column, the invention will function properly.

The dimensions of the thermally insulated apparatus can vary significantly depending on the particular column it is designed to fit, as well as on the particular column compartment configuration of various LC systems. In certain embodiments, the thermally insulated apparatus has a length of at least about 50% of the length of the column, in preferred embodiments the thermally insulated apparatus has a length of at least about 60%, 65%, 70%, 75%, 80%, 85%, or 90% of the length of the column. In a more preferred embodiment, the length of the thermally insulated apparatus is from at least about 95% of the length of the column to about 120% of the length of the column. In another more preferred embodiment, the length of the thermally insulated apparatus is greater than the length of the column. In these above described more preferred embodiments, the length of the thermally insulated apparatus (i.e., from about 95% to greater than the length of the column) allow for cap ends. These cap ends are preferably designed to fit on the opposing longitudinal ends of the thermally insulated apparatus, and are detachable. The cap ends can comprise any material(s) that are stable over the intended set temperature range of the heating source or means, and include non-limiting examples as high-density/high-melting polymers and plastics, wood, metal, ceramics, rubber, rubber polymers, rubber compounds, foam, gel materials, resins, paper and glass. Preferably, the cap ends comprise a rubber insulating material. In one variation of this embodiment, the rubber insulating material comprises an opening, for example, a slit cut half way down the cap, that can allow tubing carrying mobile phase and/or sample to pass therethrough.

As noted above, the dimensions of the thermally insulated apparatus should be selected to allow it to receive a particular chromatography column within the hollow portion of the metallic body. However, the size of the particular column compartment of the chromatography system is just as important to the dimension selection. That is, the dimensions of the thermally insulated apparatus are also selected to allow the apparatus to fit within a column compartment of the particular chromatography system used. One of skill in the art can readily determine the important dimension considerations in light of of the column compartment-thermally insulated apparatus arrangement.

The dimension of the hollow interior portion of the elongated metallic body is proportioned to accommodate the diameter of the column it is designed to insulate. While in some embodiments the inner surface of the hollow interior portion contacts a substantial portion of the outer surface of the column, the invention can function properly with a minimal amount of such surface-to-surface contact. For example, the invention encompasses a thermally insulated apparatus comprising an elongated metallic body having a cylindrically-shaped hollow interior portion that comprises dimensions that allow it to fit loosely around the column, so that it appears to "hang" on the column. This would have a minimal amount of surface-to-surface contact, whereas a differently shaped or dimensioned hollow interior portion would provide more surface to surface contact (e.g., triangular hollow interior portion would allow for 2 "surface contact points" or tightly-fitting cylindrical hollow interior portion could allow for infinite "surface contact points"). Other variations to the arrangement of the contact(s) between the inner surface of the hollow interior portion of the insulating apparatus and the outer surface of the column allow the invention to function, and will be recognized by those of skill in the art.

The elongated metallic body can circumferentially completely enclose or encircle the particular column to be insulated (i.e., in the shortest column dimension, typically the radial dimension). Alternatively, the elongated metallic body can merely substantially enclose or contain the particular column to be insulated. For example, the elongated metallic body can have a gap running along the entirety of its length, resulting in a "C" type shape when viewed from one end. This shape can allow for easier and faster removal of the thermally insulated apparatus from the column as well as allowing for a single thermally insulated apparatus to be used for a variety of column sizes, since this design can expand to some degree. Additionally, this allows for direct column exposure to a heating source or means, which can allow for faster, but perhaps less efficient heat transfer through the column, while keeping the beneficial insulation characteristics of the thermally insulated apparatus. A number of variations can be made to the elongated metallic body that are encompassed within the scope of the invention such as, for example, elongated metallic body shapes having holes, perforations, gaps, (each of which can provide for circulation of air); dimples; protrusions; waves; ridges; fins; and the like each of which can be oriented either inward and outward. Most importantly, the shape and design of the thermally insulated apparatus allows for thermal insulation of the chromatographic column, including minimizing or eliminating temperature gradients between: the interior and exterior column surfaces and the interior (stationary phase) of the column; the stationary phase and the mobile phase (including sample/analyte); the longitudinal axis of the column (both interior packing material/stationary phase and exterior surface(s)); the radial axis of the column; and the column temperature and the thermal set point of the heating means. The elongated metallic body is made from a conductive material, preferably metal selected from the non-limiting examples of copper, aluminum, steel, stainless steel, silver, gold, platinum, zinc, iron, tungsten, molybdenum, any metal alloys, any electro-plated metal, and the like. Among these metals, copper is most preferred because it is very common, has excellent conductive properties, and is relatively economical.

The insulating material contacts the outer surface of the elongated metallic body. In certain embodiments, the insulating material is permanently affixed to the outer surface, while in certain other embodiments, the insulating material is removably attached to the outer surface. The insulating material can circumferentially surround the elongated metallic body; however in certain embodiments the insulating material at least partially surrounds the elongated metallic body. In yet further embodiments, the thermally insulated apparatus comprises insulation material that is sectioned so that at least part of the insulation material is permanently affixed to outer surface of the elongated metallic body, and at least part of the insulation material is removably attached to the outer surface of the elongated metallic body. The insulation material can be any type of insulation that is used in common articles, such as automobiles, refrigerators, air conditioners, heat exchangers, and heaters, but is preferably selected from fiberglass insulation; foam insulation, for example polyethylene foam; plastics, rubber, shrink tubing, electroplated materials, resins, leather, cloth, paper, wood, rubber polymers, rubber compounds, and the like.

In certain embodiments, the thermally insulated apparatus includes an inlet for mobile phase so that mobile phase can flow from a source to the liquid chromatography column. Conduits for transporting the mobile phase through the system are preferably durable and are relatively immune to degradation effects caused by various mobile phases and more particularly to degradation effects caused by elevated temperatures. Such conduit materials include, for example, stainless steel, titanium, Hastelloy C-22, aluminum, any metal alloys, PEEK tubing, or any other material resistant to degradation or other reactive conditions. The thermally insulated apparatus can include space in its interior portion for the mobile phase conduit, so that the entirety of the column and conduit are within the interior portion of the apparatus, and thus, are at the thermal set point and free from temperature gradients. Optional end caps, preferably comprising insulating material and an opening through which the mobile phase conduit can fit, can be used to further insulate the column and mobile phase conduit. The end caps are preferably removably attached to the elongated metallic body. The end caps can be designed to fit flush with the opposing longitudinal openings of the elongated metallic body (e.g., like a flap); or be designed to extend and add length to the elongated metallic body (e.g., a cup-like structure that fits over the outer surface of the elongated metallic body); or be designed to fit within the existing length of the elongated metallic body (e.g., a rubber stopper). The end caps can also comprise a structural support such as, for example, those made from plastic (e.g., various high-density polymers, fiberglass, rubber, rubber polymers); metal (e.g., steel, stainless steel, aluminum, alloys, copper, zinc, titanium, tungsten, and the like); and wood. The structural support can be any shape (e.g., solid, mesh, round, square, etc.) as long as it can support the insulating material.

In one embodiment the thermally insulated apparatus is used in combination with a heating means. The heating means can be any heating means that is well known in the art, including, for example, radiant/convection, conductive, Peltier heaters, Peltier coolers, electrical heater coils, heated circulated air, direct electrical heating, heating element/thermocouple into a metal block, and the like. In a preferred embodiment, the thermally insulated apparatus is used in combination with a radiant or convection oven. When the thermally insulated apparatus is used in combination with a heating source or means, the design of the heating source can be used to determine the amount and location of the insulating material that contacts the outer surface of the metallic body. For example, if a heating source comprises one or a plurality of heating fins in a particular formation that transfer heat through contact, the insulating material surrounding the metallic body is preferably removed from those areas of the outer surface of the metallic body that would contact the one or plurality of fins. The insulating material remains over portions of the metallic body that do not contact the one or plurality of fins (contact gaps), providing insulation and a more stable temperature within the thermally insulated apparatus. Thus, the location, size, and type of heating source elements in a column compartment can dictate the areas of the thermally insulated apparatus that comprise insulating material on the outer surface of the metallic body.

In an aspect, the invention provides a thermally insulated apparatus for liquid chromatographic separation columns, wherein the thermally insulated apparatus reduces or eliminates differences between the desired thermal set point and the actual column temperature. In certain embodiments of the present invention, the thermally insulated apparatus is configured such that the column is at least substantially surrounded by the apparatus. This configuration maintains a constant temperature throughout the column's length and width, which, in turn, is consistent with the temperature set point of the mobile phase entering and exiting the column. Thus, the thermally insulated apparatus maintains a substantially adiabatic environment between the column and the mobile phase passing therethrough.

The thermally insulated apparatus can be designed for use with any type of chromatography column. In one aspect, the invention provides a combination of the thermally insulated apparatus as described herein, and a chromatography column. The chromatography column can be from any manufacturer, for use in a number of chromatographic applications such as, for example, HPLC, FPLC, flash chromatography, size-exclusion chromatography, and gas chromatography. Non-limiting examples of columns encompassed by this embodiment of the invention include those manufactured by Agilent, Phenomenex, Applied Bioscience, Varian Polaris, YMC, Tosohaas, VYDAC, Dionex, TSK Co., Source, TOSOH Biosep, Pharmacia Biotech, POLY LC, SK 5pw, Resource, and PLRP-S. Such columns are well known to those of skill in the art, and can be reviewed in the manufacturer's sales information and/or catalogs. Non-limiting examples of preferred columns include Zorbax 300sb-C18, 3.5 microns, 4.6×150 mm (Agilent); Poly 4.6 mm id×150 mm 5 micron, 200 Å pore size (Polymer Labs); and C4 bonded phase silica column, 4.6 mm id×150 mm, 5 microns, 300 Å pore size (YMC).

The thermally insulated apparatus can be designed for use with any type of chromatography column compartment. In one aspect, the invention provides a combination of the thermally insulated apparatus and a chromatography column compartment. The chromatography column compartment can be from any manufacturer and the important aspects of the compartment are available from the manufacturer's literature (e.g., dimensions, heating means, etc.). One non-limiting examples of column compartments encompassed by this embodiment of the invention include those manufactured by Agilent, such as the 1100 and 1200. The column compartments are typically used to maintain a desired set point temperature for chromatographic separations and/or analysis. The way in which a particular column compartment maintains a set point temperature is not critical to the claimed invention, as the thermally insulated apparatus can be modified for use in any such column compartment. For example, the amount and/or location of the insulating material can be controlled based on the method of heat transfer and/or the arrangement of the heating means in a column compartment. One skilled in the art will recognize that the thermally insulated apparatus will function as long as a heating source can contact a portion of the metallic body, while the insulating material covers the remainder of the metallic body that is not in contact with the heating source (contact gaps).

The size of column compartments can vary and are available from the manufacturer's literature. Therefore, the size of the thermally insulated apparatus can very according to the particular column compartment used with a chromatography system. For example, the Agilent 1100 column compartment has approximate exterior dimensions of 5.5 inches (width) and 16 inches (length), and an interior dimension that is divided by heating fins into three sections of about ⅞ inches (width) and about 11-12 inches (length). A thermally insulated apparatus would be designed based on these dimensions (for example, see the description of the prototypes 1-4 in the Examples). Thus, a thermally insulated apparatus of the invention comprises a size that allows the apparatus to fit within the particular column compartment of the chromatography system.

The following examples are provided merely in order to illustrate particular embodiments of the invention, and while they are described with particular language and may relate to specific aspects of the invention, they should not be considered as limiting the invention defined by the appended claims. It should be understood that the invention can be carried out in a number of specifically different ways that comprise various modifications, without departing from the scope and spirit of the invention as defined in the appended claims.

EXAMPLES

Example 1

Construction of Thermally Insulated Cylindrical Apparatus

Several prototypes of the thermally insulated apparatus have been constructed as follows.

Prototype One:

Prototype one (1) was constructed by cutting a ⅞ inch diameter/width copper tube to 11½ inches length (McMaster-Carr Catalog #8967K85 Tubing size: ¾ inch, OD: ⅞ inch, ID: 0.811 inch, Wall: 0.032 inch. Liquid (quick dry) insulation plastic (Plastic Dip, Performix, multi-purpose rubber coating, blue) was applied to the entire tube and allowed to dry. Some of the insulation plastic was then cut away to allow the copper tube to have direct contact with the heating fins of an Agilent 1100 column compartment. By removing only the portions of plastic insulation that would allow metal-to-metal (e.g., metallic body of thermally insulated apparatus to heating fin) contact while keeping the remaining insulation in place, the tube was heated to the correct temperature (set point), and the insulating plastic kept the air temperature in the tube stable. Rubber end caps were fashioned out of rubber stoppers (VWR International, Catalog #59580-149, size 3 m29 solid). Two rubber stoppers were cut in half (radial axis) and a slit was cut half way through (longitudinal axis). The slits allow the lines carrying the mobile phase to and from the column to enter and exit the thermally insulated apparatus. The length and diameter of prototype 1 was designed based on the dimensions of the Agilent 1100 column compartment. The tube can be a different length and/or diameter depending on the dimensions of the heating source in various manufacturer's column compartments. Prototype 1 improved the temperature characteristics of the chromatographic column but still had a significant difference with set point of the column compartment heater.

Prototype Two:

Prototype two (2) was created using the same dimensions and copper tubing used in prototype one (McMaster-Carr Catalog #8967K85). However, in an effort to decrease the difference between the chromatographic column temperature and the column compartment heater set point different insulation material was used. The insulating material was spongy insulating foam (McMaster-Carr, Spongy foam insulation sheet). The spongy foam insulation was cut to fit the copper tube and then additional pieces were cut away to allow the copper tube to have direct contact with the heating fins of the Agilent 1100 column compartment. By removing only the portions of foam insulation that allow for metal-to-metal contact and keeping the rest of the insulation in place, the tube was heated to the correct temperature and the insulating foam kept the air temperature in the tube stable. The insulation was attached to the copper tube with double-sided tape that can withstand an 80° C. temperature. Rubber end caps were fashioned out of rubber stoppers (VWR International, Catalog #59580-149), as described for prototype 1 above. Prototype two gave excellent results and providing $\leq \pm 1°$ C. difference in column temperature compared to column compartment set point. However the foam was difficult to shape and tended to flake off in pieces.

Prototype Three:

Prototype three (3) was created using the same dimension of copper tubing used in prototype one (McMaster-Carr Catalog #8967K85). The insulating material was different in an effort to reduce the difference between the chromatographic column temperature and the column compartment heater set point. For this prototype, the insulating material was a shrink-wrap/glue adhesive plastic insulation (Electrical Terminal Service, Part# X700-200, red). The insulation was wrapped around the copper tube and heated to 500° C. with a heat gun for 30 min., or until the insulation shrank and its glue bonded to the copper tube. The insulation was then cut away with a razor blade and dremel tool to allow the copper tube to have direct contact with the heating fins of the Agilent 1100 column compartment. By removing portions of plastic insulation that allow for metal-to-metal contact and keeping the rest of the insulation in place, the tube heated to the correct temperature and the insulating plastic kept the air temperature in the tube stable. Rubber end caps were fashioned out of rubber stoppers as described for prototypes 1 and 2 (VWR International, Catalog #59580-149). Prototype three failed to improve the column temperature characteristics, therefore it was decided to go back to prototype 2 and use an improved foam insulation.

Prototype Four:

Prototype four was created using the same dimension of copper tubing used in prototypes 1-3 (McMaster-Carr Catalog #8967K85), but with different insulating material than prototype 2. For this prototype, the insulating material was foam used for insulating refrigeration lines (Polyethylene foam and tube insulation, (McMaster-Carr Catalog #4734K115, insulation ID: ⅞ inch, temperature rated −17.8° C. to 82.2° C.). The foam insulation was cut to fit the copper tube and then additional pieces were cut away to allow the copper tube to have direct contact with the heating fins of the Agilent 1100 column compartment. This arrangement allowed the tube to be heated to the correct temperature, while the insulating foam kept the air temperature in the tube stable. The insulation was attached to the copper tube with double-sided tape that can withstand an 80° C. temperature. Rubber end caps were fashioned out of rubber stoppers as described for the previous prototypes (VWR International, Catalog #59580-149). Prototype four gave the best insulating results, and its foam insulation was stable.

Example 2

Insulating Capacity and Temperature Stabilization of Prototypes 1-4

Prototypes 1-4 were constructed as described generally in Example 1. These prototypes were designed to fit an Agilent 1100 column compartment (see product performance specifications for more details, including column compartment dimensions, Agilent Technologies, Palo Alto, Calif.). The Agilent column compartment has two Peltier heater/cooling assemblies (a left and a right). Each one has four fins that protrude out and provide three shelves for the chromatographic columns to rest on. A large area having no heating block is located between the two Peltier assemblies. The liquid mobile phase first flows through the Peltier heater/cooling assembly, which equilibrates the liquid mobile phase to the set point temperature prior to entering the column. Even though the liquid mobile phase is heated before going through the column, the instability of the air and column temperature causes temperature gradients and unstable/incorrect temperature readings within the column and air temperature surrounding the column. The prototypes 1-4 are designed to fit on any one of the three shelves of the Agilent system, or they can be modified to fit in combination on all three shelves with three different thermally insulated apparatuses.

Comparative Data

The temperature set point was at 60° C. and temperature readings were recorded using a calibrated temperature sensor taped to the column after at least 1 hr at the set point. In addition there was no flow of mobile phase through the column. This was the first set of tests to get a baseline reading on the efficiencies or deficiencies of the system.

| Column assembly | Set point (° C.) | Actual column temp. (° C.) |
|---|---|---|
| Column alone | 60.0 | 34.09 |
| Column with cover | 60.0 | 43.73 |
| Column alone with aluminum foil cover | 60.0 | 43.0 |
| Column with cover and with aluminum foil cover | 60.0 | 50.5 |
| Prototype 1 Insulated tube w/o cover | 60.0 | 52.0 |
| Prototype 1 Insulated tube with cover. Placed on the middle shelf of column compartment | 60.0 | 57.5 |
| Prototype 1 Insulated tube with cover. Placed on lower column compartment shelf | 60.0 | 55.4 |
| Prototype 1 Insulated tube with cover and insulation on cover. Placed on the middle shelf of column compartment | 60.0 | 59.3 |
| Prototype 1 Insulated tube with cover and insulation on cover. Placed on lower column compartment shelf | 60.0 | 58.1 |

| Conditions | | Temp ° C. of column | Temp ° C. of inside air |
|---|---|---|---|
| Prototype 4 Data | | | |
| No column flow; No 2 m SSC; No heated mobile phase; and TIC installed | Average | 15.127 | 15.127 |
| | Diff from 15° C. | −0.127 | −0.127 |
| | Average | 39.403 | 39.323 |
| | Diff from 40° C. | 0.597 | 0.677 |
| | Average | 59.069 | 58.943 |
| | Diff from 60° C. | 0.931 | 1.057 |
| | Average | 78.913 | 78.744 |
| | Diff from 80° C. | 1.087 | 1.256 |
| 0.5 ml/min column flow; No 2 m SSC; No heated mobile phase; TIC installed; | Average | 16.048 | 15.688 |
| | Diff from 15° C. | −1.048 | −0.688 |
| | Average | 37.508 | 38.672 |
| | Diff from 40° C. | 2.492 | 1.328 |
| | Average | 55.021 | 57.423 |
| | Diff from 60° C. | 4.979 | 2.577 |
| | Average | 72.590 | 76.378 |
| | Diff from 80° C. | 7.410 | 3.622 |
| 1.0 ml/min column flow; No 2 m SSC; No heated mobile phase; TIC installed; | Average | 17.056 | 16.487 |
| | Diff from 15° C. | −2.056 | −1.487 |
| | Average | 34.821 | 37.412 |
| | Diff from 40° C. | 5.179 | 2.588 |
| | Average | 49.414 | 54.751 |
| | Diff from 60° C. | 10.586 | 5.249 |
| | Average | 63.598 | 72.216 |
| | Diff from 80° C. | 16.402 | 7.784 |
| 1.0 ml/min column flow; 2 m SSC installed; 2 m SSC heated on the bottom fin No heated mobile phase TIC installed | Average | 16.153 | 15.957 |
| | Diff from 15° C. | −1.153 | −0.957 |
| | Average | 38.560 | 38.868 |
| | Diff from 40° C. | 1.440 | 1.132 |
| | Average | 56.988 | 57.603 |
| | Diff from 60° C. | 3.012 | 2.397 |
| | Average | 75.872 | 76.487 |
| | Diff from 80° C. | 4.128 | 3.513 |
| 1.0 ml/min column flow 2 m SSC installed 2 m SSC heated behind TIC No heated mobile phase TIC installed | Average | 15.330 | 15.461 |
| | Diff from 15° C. | −0.330 | −0.461 |
| | Average | 38.952 | 38.691 |
| | Diff from 40° C. | 1.048 | 1.309 |
| | Average | 58.154 | 57.552 |
| | Diff from 60° C. | 1.846 | 2.448 |
| | Average | 76.990 | 76.460 |
| | Diff from 80° C. | 3.010 | 3.540 |
| 1.0 ml/min column flow 2 m SSC installed 2 m SSC heated inside/outside of TIC No heated mobile phase TIC installed | Average | 16.915 | 16.534 |
| | Diff from 15° C. | −1.915 | −1.534 |
| | Average | 36.947 | 37.590 |
| | Diff from 40° C. | 3.053 | 2.410 |
| | Average | 53.664 | 55.174 |
| | Diff from 60° C. | 6.336 | 4.826 |
| | Average | 71.079 | 74.169 |
| | Diff from 80° C. | 8.921 | 5.831 |
| 1.0 ml/min column flow 2 m SSC installed | Average | 15.986 | 15.499 |
| | Diff from 15° C. | −0.986 | −0.499 |

-continued

Prototype 4 Data

| Conditions | | Temp °C. of column | Temp °C. of inside air |
|---|---|---|---|
| 2 m SSC heated inside of the TIC | Average | 40.028 | 39.886 |
| | Diff from 40° C. | −0.028 | 0.114 |
| 6 ul mobile phase heater utilized | Average | 59.580 | 59.962 |
| | Diff from 60° C. | 0.420 | 0.038 |
| TIC installed | Average | 79.220 | 79.415 |
| | Diff from 80° C. | 0.780 | 0.585 |
| 1.0 ml/min column flow | Average | 15.605 | 15.231 |
| No 2 m SSC installed | Diff from 15° C. | −0.605 | −0.231 |
| 6 ul mobile phase heater utilized | Average | 40.104 | 39.686 |
| | Diff from 40° C. | −0.104 | 0.314 |
| TIC installed | Average | 59.876 | 59.400 |
| | Diff from 60° C. | 0.124 | 0.600 |
| | Average | 79.689 | 79.095 |
| | Diff from 80° C. | 0.311 | 0.905 |
| 1.0 ml/min column flow | Average | 15.629 | 15.199 |
| No 2 m SSC installed | Diff from 15° C. | −0.629 | −0.199 |
| 6 ul mobile phase heater utilized | Average | 40.114 | 39.639 |
| | Diff from 40° C. | −0.114 | 0.361 |
| TIC installed | Average | 59.876 | 59.280 |
| | Diff from 60° C. | 0.124 | 0.720 |
| | Average | 79.606 | 78.814 |
| | Diff from 80° C. | 0.394 | 1.186 |

Legend: 2 m SSC = 2 meter stainless steel Capillary; TIC = Thermally Insulated Cylindrical Apparatus Data Summary:

The first test had no column flow, no 2 m Stainless Steel Capillary (SSC) and no mobile phase heating. The largest average temperature difference between set point and actual was less than 1.087° C. from four different temperatures 15° C., 40° C., 60° C. and 80° C. The largest average air temperature difference between set point and actual was less than 1.256° C. from four different temperatures 15° C., 40° C., 60° C. and 80° C.

The second test had 0.5 ml/min column flow, no 2 m Stainless Steel Capillary (SSC) and no mobile phase heating. The largest average temperature difference between set point and actual was less than 7.410° C. from four different temperatures 15° C., 40° C., 60° C. and 80° C. The largest average air temperature difference between set point and actual was less than 3.622° C. from four different temperatures 15° C., 40° C., 60° C. and 80° C.

The difference between the first and second tests was the introduction of the flow of liquid mobile phase through the column. The room temperature flow decreased the temperature of the column. The column temperature difference was affected more as the temperature of the column was increased.

The third test had 1.0 ml/min column flow, no 2 m Stainless Steel Capillary (SSC) and no mobile phase heating. The largest average temperature difference between set point and actual was less than 16.402° C. from four different temperatures 15° C., 40° C., 60° C. and 80° C. The largest average air temperature difference between set point and actual was less than 7.784° C. from four different temperatures 15° C., 40° C., 60° C. and 80° C.

The difference between the second and third tests was the increase of column flow rate to 1 mL/min. The increase of column flow resulted in a much greater temperature difference between set point and actual temperature. The greatest difference was 16.402° C. from set point.

The fourth test had 1.0 ml/min column flow, 2 m Stainless Steel Capillary (SSC) installed and heated on the bottom fin of the column compartment, and no mobile phase heating. The largest average temperature difference between set point and actual was less than 4.128° C. from four different temperatures 15° C., 40° C., 60° C. and 80° C. The largest average air temperature difference between set point and actual was less than 3.513° C. from four different temperatures 15° C., 40° C., 60° C. and 80° C.

The temperature difference improvement in test 4 compared to test 3 was due in part to the heating of the 2 meters of stainless steel capillary before the TIC. The heating of the 2 meters of stainless steel capillary heats the mobile phase before going into the column thus reducing the temperature decrease of the column.

The fifth test had 1.0 ml/min column flow, 2 m Stainless Steel Capillary (SSC) installed and heated behind the TIC and no mobile phase heating. The largest average temperature difference between set point and actual was less than 3.010° C. from four different temperatures 15° C., 40° C., 60° C. and 80° C. The largest average air temperature difference between set point and actual was less than 3.540° C. from four different temperatures 15° C., 40° C., 60° C. and 80° C.

The temperature difference improvement of test 5 compared to test 4 was due in part to more efficient heating of the 2 meters of stainless steel capillary behind the TIC. The difference in column temperature dropped to less than 3.010° C. from 4.128° C.

The sixth test had 1.0 ml/min column flow, 2 m Stainless Steel Capillary (SSC) installed and heated inside and outside of the TIC and no mobile phase heating. The largest average temperature difference between set point and actual was less than 8.921° C. from four different temperatures 15° C., 40° C., 60° C. and 80° C. The largest average air temperature difference between set point and actual was less than 5.831° C. from four different temperatures 15° C., 40° C., 60° C. and 80° C.

The decrease in performance of test 6 compared to test 5 was due in part to the less efficient heating of the 2 meters of stainless steel capillary before the TIC. The heating of the 2 meters of stainless steel capillary was inefficient and exposing the 2 m SSC to the temperature outside the TIC caused the air temperature of the TIC to decrease as well.

The seventh test had 1.0 ml/min column flow, 2 m Stainless Steel Capillary (SSC) installed and heated inside the TIC and 6 µL of mobile phase heating of the column compartment. The largest average temperature difference between set point and actual was less than 0.986° C. from four different temperatures 15° C., 40° C., 60° C. and 80° C. The largest average air temperature difference between set point and actual was less than 0.585° C. from four different temperatures 15° C., 40° C., 60° C. and 80° C.

The seventh test had improved results compared to all prior tests. The added step of heating the 6 µL of mobile phase by the column compartment helped reduce the difference set point and actual temperature. The column temperature dropped from 3.010° C. to 0.986° C.

The eighth test had 1.0 mL/min column flow, no 2 m Stainless Steel Capillary (SSC) installed and 6 µL of mobile phase heating of the column compartment. The largest average temperature difference between set point and actual was less than 0.605° C. from four different temperatures 15° C., 40° C., 60° C. and 80° C. The largest average air temperature difference between set point and actual was less than 0.905° C. from four different temperatures 15° C., 40° C., 60° C. and 80° C.

The eighth test gave the best overall result. The TIC with the 6 µL mobile phase heater from the column compartment is the optimum configuration that was tested.

The ninth test had the same parameters and conditions as item 8. The largest average temperature difference between set point and actual was less 0.629° C. from four different temperatures 15° C., 40° C., 60° C. and 80° C. The largest average air temperature difference between set point and actual was less than 1.186° C. from four different temperatures 15° C., 40° C., 60° C. and 80° C.

The data demonstrates that under these conditions the thermally insulation cylindrical apparatus, in combination with the 6 µL mobile phase heater of the column compartment yields the smallest difference between the column temperature set point verses the actual temperature.

We claim:

1. A thermally insulated apparatus, comprising:
   (a) an elongated metallic body having an exterior portion, a hollow interior portion and two openings located at opposing ends of a longitudinal axis;
   (b) an insulating material contacting the exterior of the elongated metallic body of (a); and
   (c) two capping members having a design that allows the capping members to substantially cover the openings located at opposing ends of the longitudinal axis of the metallic body of (a), and
       wherein each of the two capping members comprise an opening or slit that allows tubing, which carries mobile phase into and out of a analytical separation column, to pass therethrough,
   wherein the insulation material substantially surrounds the entire outer surface of the elongated metallic body with the exception of those portions that contact a heating source.

2. The thermally insulated apparatus of claim 1 further including a chromatography column situated within the elongated metallic body of the thermally insulated apparatus.

3. The thermally insulated apparatus of claim 2, wherein the column is 300sb-C18, 3.5 micron, 4.6×150 mm; Poly 4.6 mm id×150 mm, 5 micron, 200 Å pore size; or C4 bonded phase silica column, 4.6 mm id×150 mm, 5 micron, 300 Å pore size.

4. The thermally insulated apparatus of claim 1 having a size such that it may be placed within a chromatography column compartment of a liquid chromatography system.

5. A method for maintaining an elevated set point temperature in liquid chromatography applications comprising:
   (a) providing a mobile phase inlet conduit configured to convey mobile phase from a mobile phase source to a chromatographic column;
   (b) providing a pre-heater apparatus operably coupled to said mobile phase inlet conduit for heating the mobile phase to an elevated set point temperature;
   (c) providing a chromatographic column operably coupled to, and disposed downstream from, said pre-heater apparatus such that the mobile phase exiting said pre-heater apparatus is directed to said column, said column including the thermally insulated apparatus of claim 1 for maintaining said column at temperatures consistent set point temperature of the mobile phase; and
   (d) chromatographically separating the liquid mobile phase in said column at an elevated temperature maintained in a substantially adiabatic state throughout an entire length of said column.

6. A thermally insulated apparatus comprising:
   (a) an elongated, cylindrical copper tube having a hollow interior portion and two openings located at opposing ends of a longitudinal axis;
   (b) a polyethylene foam insulating material contacting the outer surface of the copper tube of (a), wherein the polyethylene foam is removed from portions of the outer surface of the copper tube in areas that contact a heating source; and
   (c) two capping members having a design that allows the capping members to substantially cover the openings located at opposing ends of the longitudinal axis of the metallic cylindrical tube of (a), and
       wherein each of the two capping members comprise an opening or slit that allows tubing, which carries mobile phase into and out of the analytical separation column, to pass therethrough;
   wherein the thermally insulated apparatus has a size that allows it to fit within the column compartment of a liquid chromatography system.

* * * * *

UNITED STATES PATENT AND TRADEMARK OFFICE
CERTIFICATE OF CORRECTION

| | | |
|---|---|---|
| PATENT NO. | : 7,735,525 B2 | Page 1 of 1 |
| APPLICATION NO. | : 11/559809 | |
| DATED | : June 15, 2010 | |
| INVENTOR(S) | : Christopher J. R. Paszty | |

It is certified that error appears in the above-identified patent and that said Letters Patent is hereby corrected as shown below:

Column 14, Line 14:

"...temperatures consistent set.." should be corrected to read --temperatures consisting with the set--.

Signed and Sealed this
Twenty-third Day of October, 2012

David J. Kappos
*Director of the United States Patent and Trademark Office*